(12) United States Patent
Wang

(10) Patent No.: US 7,579,336 B2
(45) Date of Patent: Aug. 25, 2009

(54) PHARMACEUTICAL COMPOSITION COMPRISING TEMOZOLOMIDE ESTER

(75) Inventor: Yongfeng Wang, Tianjin (CN)

(73) Assignee: Tian Jin Tasly Group Co., Ltd., Tianjin (CN)

( * ) Notice: Subject to any disclaimer, the term of this patent is extended or adjusted under 35 U.S.C. 154(b) by 0 days.

(21) Appl. No.: 11/575,849

(22) PCT Filed: Sep. 15, 2005

(86) PCT No.: PCT/CN2005/001477

§ 371 (c)(1),
(2), (4) Date: Mar. 22, 2007

(87) PCT Pub. No.: WO2006/032190

PCT Pub. Date: Mar. 30, 2006

(65) Prior Publication Data

US 2008/0044457 A1  Feb. 21, 2008

(30) Foreign Application Priority Data

Sep. 22, 2004  (CN) .......... 2004 1 0072056

(51) Int. Cl.
*A61K 31/4188* (2006.01)
*A61P 35/00* (2006.01)
*C07D 487/04* (2006.01)

(52) U.S. Cl. .......... 514/183; 544/179
(58) Field of Classification Search .......... 544/179; 514/183

See application file for complete search history.

(56) References Cited

U.S. PATENT DOCUMENTS 7,173,021 B2 * 2/2007 Wang et al. .......... 514/183

* cited by examiner

*Primary Examiner*—Venkataraman Balasubramanian
(74) *Attorney, Agent, or Firm*—Michael L. Greenberg, Esq.; Greenberg & Lieberman, LLC

(57) ABSTRACT

The present invention discloses general formula I of Temozolomide-8-carboxylate compounds, the process for preparation, pharmaceutical compositions comprising the compounds and the use of the compounds and pharmaceutical compositions for the manufacture of an antitumor medicament. The said pharmaceutical composition comprises one or more general formula I Temozolomide-8-carboxylate compounds as active ingredient, together with conventional pharmaceutical carriers. The composition also comprises one or more pharmaceutically acceptable acidic material, optionally second or tertiary alcohol or ester or ether derivatives thereof. The said pharmaceutical composition can be made into various common formulations, particularly oral formulations as well as topically transdermal patches. The present invention also discloses the application of the compounds and the compositions to treat tumor.

16 Claims, 2 Drawing Sheets

PHARMACEUTICAL COMPOSITION COMPRISING TEMOZOLOMIDE ESTER

FIELD OF INVENTION

The present invention relates to the field of medicine. More specifically, the present invention relates to Temozolomide-8-carboxylate derivatives, method for preparing it, compositions comprising them and the use of the derivatives and compositions in the manufacture of a medicament for treatment of tumor, in particular to the use of the compound and the composition in an oral and transdermal preparation for treatment of tumor such as skin carcinoma, brain carcinoma and lymphoma.

BACKGROUND ART

Temozolomide (hereinafter referred to as "TMZ"), an alkylating agent for treatment of carcinoma, has a broad-spectrum bioactivity of anti-tumor [L. H. Tsang, et al. Cancer Chemother Pharmacol. 27 (1991): 342-346], which in particular has bioactivity for treatment neuroglioma (brain carcinoma) and malignant melanoma (skin carcinoma). In some western countries, the TMZ capsule had been approved to be used for the treatment of malignant neuroglioma. WO 0057867 described a method by using TMZ at a cyclical schedule. Also, the TMZ capsule has been approved to be used clinically in China. Phase II clinical trials showed that TMZ had activity for curing malignant melanoma [N. M. Bleehen, et al. J. Clin. Oncol. 13 (1995): 910-913], and recent phase III clinical trials revealed that TMZ has the same activity as the dacarbazine for curing malignant melanoma [M. R. Middleton, et al. J. Clin. Oncol. 18 (2000): 158-166] even with the similar side effects between them such as leucocytopenia, nausea, vomit, hair loss, red rash and constipation. Besides, oral administration of TMZ displayed dose-limiting myelotoxicity [A. M. Heimberger, et al. Clin. Can. Res. 6 (2000): 4148-4153]. Previous study on changing formulation exhibited that intrathecal injection administration of TMZ solution could decrease the side effects [J. H. Sampson, et al. Clin. Can. Res. 5 (1999): 1183-1188]. So it should be deemed that the transdermal formulation is the ideal for TMZ to cure skin carcinoma, especially during the early period. Some studies have proven that local administration of toremifene on site of carcinoma might result in a high local concentration, while lowering the systematic concentration [L. Soe, et al. Cancer Chemother. Pharmacol., 39 (1997): 513-520], which brought about lower systematic toxicity.

Generally, percutaneous administration is conditioned by both the skin barrier and the physicochemical properties of drug. Instability and insolubility of said drug prevent it from being made into formulations. Studies, as published in WO0057867, showed that its inability to permeate artificial skin (silicon membrane), rat skin and human skin rendered it impossible to be made into transdermal formulations. In view of this, the application of TMZ will be limited to a great extent.

Previously, aiming at structure modification, a lot of derivatives has been synthesized, most of which were focused on replacement of substitute group at nitrogen atom of No. 3 and the modification of substitute group at nitrogen atom of amide group of No. 8. The general formula, as described in EP0252682 (1987), claimed methyl, ethyl, propyl and butyl temozolomide-8-carboxylates, but didn't disclose their pharmacological actions and the activities for treatment of carcinomas.

On the other hand, the compounds of imidazo[5,1-d]-1,2,3,5-tetrazin-4-one, typically represented by TMZ, share a common trait of so bad solubility, that they can hardly be dissolved in any common-used solvents such as ethyl acetate, dichloromethane and water. They exhibit a slight solubility of about 1~5% in the blend of organic solvent and water, for example the aqueous solution of acetic acid, acetonitrile, acetone, methanol or ethanol with the concentration of 1~10%. Even in the non-protonic polar solvent-DMSO, their solubility is about 5%. In addition, another trait of these compounds is their instability, which is embodied not simply by their sensibility to light, what is more, by their sensibility to alkaline mediums with pH value more than 7 and those mediums with nucleophilic group such as the compounds containing amidogen, hydroxyl and mercapto group. For example, the environment of the pH value more than 7 will make these compounds rapidly decomposing and changing color (red); the same story may occur in the methanol and ethanol. It is therefore limited for the methanol and ethanol to be used as the solubilizer in manufacturing preparations. So it seems to be much desired to develop a novel bioactive compound and to seek the methods for enhancing its stability and solubility in the application of the pharmaceutical industry.

DETAILED DESCRIPTION OF THE INVENTION

Thus, the object of the present invention is to provide 3,4-dihydro-3-methyl-4-oxoimidazo[5,1-d]-1,2,3,5-tetrazine-8-carboxylate derivatives of the general formula (I) and the methods for preparing them, and the compositions comprising said derivatives and methods for preparing said compositions.

The inventors of the present invention found out that the 3,4-dihydro-3-methyl-4-oxoimidazo[5,1-d]-1,2,3,5-tetrazine-8-carboxylate derivatives of the general formula (I) and the compositions comprising them have the anti-tumor activity, and will be used for the treatment of carcinomas, especially for the skin carcinoma, brain carcinoma and lymphatic carcinoma etc. Thus, the other object of the invention is to provide the use of the 3,4-dihydro-3-methyl-4-oxoimidazo[5,1-d]-1,2,3,5-tetrazine-8-carboxylate derivatives of the general formula (I) and the compositions comprising them in manufacturing the drugs for treatment of carcinomas, wherein said carcinomas include skin carcinoma, brain carcinoma and lymphatic carcinoma etc.

Another object of the invention is to provide various preparations having the bioactivities of anti-tumor and comprising the temozolomide-8-carboxylate derivatives of the general formula (I) as the active ingredient(s), especially the oral preparation and topical transdermal patches (penetration skin patch). Said topical transdermal patches include matrix type controlled-release patch, solid reservoir type controlled-release patch or liquid reservoir type controlled-release patch.

The structure of said 3,4-dihydro-3-methyl-4-oxoimidazo[5,1-d]-1,2,3,5-tetrazine-8-carboxylate in the present invention is represented by the general formula (I) as follows:

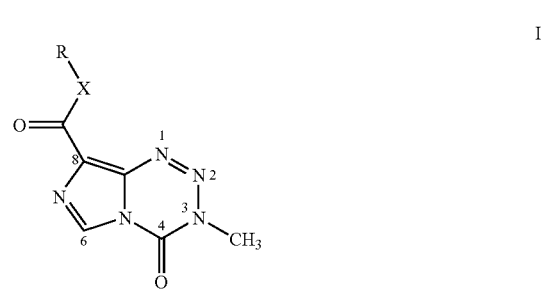

Wherein X is O or S;

R is substituted or unsubstituted C3~C10 straight or branched chain alkyl, C3~C10 cycloalkyl, C3~C10 straight or branched alkenyl or C3~C10 straight or branched chain alkynyl;

Further, R may have substituent(s), said substituent(s) may be C1~C6 alkyl, C1~C6 alkoxy, C1~C6 alkylthio group, C1~C6 alkyl amino group, phenyl or phenyl substituted by halogen.

Preferably, X is O.

In above definition, the term of C3~C10 straight or branched chain alkyl used herein is a saturated straight or branched chain hydrocarbyl having 3-10 carbon atoms, for example propyl, butyl, amyl, hexyl, heptyl, octyl, nonyl or decyl and the like, and all their isomers such as isopropyl, isobutyl, tert-butyl, iso-hexyl or iso-heptyl etc. The preferred R is selected from a group consisting of methyl, ethyl, propyl, isopropyl, n-butyl, 1-methyl-propyl, 2-methyl-propyl, amyl, 1-methyl-butyl, 2-methyl-butyl, 3-methyl-butyl, hexyl, 1-methyl-amyl, 2-methyl-amyl, 3-methyl-amyl, 4-methyl-amyl, heptyl, 1-methyl-hexyl, 2-methyl-hexyl, 3-methyl-hexyl, 4-methyl-hexyl, 5-methyl-hexyl, octyl, 1-methyl-heptyl, 2-methyl-heptyl, 3-methyl-heptyl, 4-methyl-heptyl, 5-methyl-heptyl, 6-methyl-heptyl, 1-ethyl-propyl, 1-ethyl-butyl, 1-ethyl-amyl, 2-ethyl-amyl or 3-ethyl-amyl. The more preferred R is n-hexyl, isohexyl and cylcohexyl. The most preferred R is n-hexyl.

Corresponding to the groups described above, the TMZ-8-carboxyl acid derivatives include:

Methyl 3,4-dihydro-3-methyl-4-oxoimidazo[5,1-d]-1,2,3,5-tetrazine-8-carboxylate;
Ethyl 3,4-dihydro-3-methyl-4-oxoimidazo[5,1-d]-1,2,3,5-tetrazine-8-carboxylate;
Propyl 3,4-dihydro-3-methyl-4-oxoimidazo[5,1-d]-1,2,3,5-tetrazine-8-carboxylate;
Butyl 3,4-dihydro-3-methyl-4-oxoimidazo[5,1-d]-1,2,3,5-tetrazine-8-carboxylate;
1-methyl-butyl 3,4-dihydro-3-methyl-4-oxoimidazo[5,1-d]-1,2,3,5-tetrazine-8-carboxylate;
1-ethyl-butyl 3,4-dihydro-3-methyl-4-oxoimidazo[5,1-d]-1,2,3,5-tetrazine-8-carboxylate;
1-ethyl-propyl 3,4-dihydro-3-methyl-4-oxoimidazo[5,1-d]-1,2,3,5-tetrazine-8-carboxylate;
1-ethyl-amyl 3,4-dihydro-3-methyl-4-oxoimidazo[5,1-d]-1,2,3,5-tetrazine-8-carboxylate;
1-methyl-hexyl 3,4-dihydro-3-methyl-4-oxoimidazo[5,1-d]-1,2,3,5-tetrazine-8-carboxylate;
2-methyl-hexyl 3,4-dihydro-3-methyl-4-oxoimidazo[5,1-d]-1,2,3,5-tetrazine-8-carboxylate;
3-methyl-hexyl 3,4-dihydro-3-methyl-4-oxoimidazo[5,1-d]-1,2,3,5-tetrazine-8-carboxylate;
4-methyl-hexyl 3,4-dihydro-3-methyl-4-oxoimidazo[5,1-d]-1,2,3,5-tetrazine-8-carboxylate;
5-methyl-hexyl 3,4-dihydro-3-methyl-4-oxoimidazo[5,1-d]-1,2,3,5-tetrazine-8-carboxylate;
1-methyl-heptyl 3,4-dihydro-3-methyl-4-oxoimidazo[5,1-d]-1,2,3,5-tetrazine-8-carboxylate;
2-methyl-heptyl 3,4-dihydro-3-methyl-4-oxoimidazo[5,1-d]-1,2,3,5-tetrazine-8-carboxylate;
3-methyl-heptyl 3,4-dihydro-3-methyl-4-oxoimidazo[5,1-d]-1,2,3,5-tetrazine-8-carboxylate;
4-methyl-heptyl 3,4-dihydro-3-methyl-4-oxoimidazo[5,1-d]-1,2,3,5-tetrazine-8-carboxylate;
5-methyl-heptyl 3,4-dihydro-3-methyl-4-oxoimidazo[5,1-d]-1,2,3,5-tetrazine-8-carboxylate;
6-methyl-heptyl 3,4-dihydro-3-methyl-4-oxoimidazo[5,1-d]-1,2,3,5-tetrazine-8-carboxylate;
Amyl 3,4-dihydro-3-methyl-4-oxoimidazo[5,1-d]-1,2,3,5-tetrazine-8-carboxylate;
n-hexyl 3,4-dihydro-3-methyl-4-oxoimidazo[5,1-d]-1,2,3,5-tetrazine-8-carboxylate;
Cyclohexyl 3,4-dihydro-3-methyl-4-oxoimidazo[5,1-d]-1,2,3,5-tetrazine-8-carboxylate;
Isohexyl 3,4-dihydro-3-methyl-4-oxoimidazo[5,1-d]-1,2,3,5-tetrazine-8-carboxylate;
Heptyl 3,4-dihydro-3-methyl-4-oxoimidazo[5,1-d]-1,2,3,5-tetrazine-8-carboxylate; and
Octyl 3,4-dihydro-3-methyl-4-oxoimidazo[5,1-d]-1,2,3,5-tetrazine-8-carboxylate.

The more preferred one is n-hexyl 3,4-dihydro-3-methyl-4-oxoimidazo[5,1-d]-1,2,3,5-tetrazine-8-carboxylate, isohexyl 3,4-dihydro-3-methyl-4-oxoimidazo[5,1-d]-1,2,3,5-tetrazine-8-carboxylate and cyclohexyl 3,4-dihydro-3-methyl-4-oxoimidazo[5,1-d]-1,2,3,5-tetrazine-8-carboxylate; the most preferred one is n-hexyl 3,4-dihydro-3-methyl-4-oxoimidazo[5,1-d]-1,2,3,5-tetrazine-8-carboxylate.

In the above definition of the general formula, the term of C3~C10 cycloalkyl used herein is a cyclic saturated hydrocarbyl having 3-10 carbon atoms such as cyclopropyl, cyclobutyl, cycloamyl, cyclohexyl, cycloheptyl, cyclooctyl, cyclononyl or cyclodecyl etc.

In the above definition of the general formula, the term of C3~C10 chain alkenyl refers to hydrocarbyl containing 1,2 or 3 unsaturated double-bonds and 3-10 carbon atoms such as propenyl, butenyl, pentenyl, hexenyl, heptenyl and heptadienyl etc.

In the above definition of the general formula, the term of C3~C10 chain alkynyl refers to hydrocarbyl containing 1,2 or 3 unsaturated triple-bonds and 3-10 carbon atoms such as propynyl, butynyl, pentynyl, hexynyl and heptynyl etc.

In the above definition of the general formula, the term of C1~C6 alkyl, as defined above, refers to straight or branched chain alkyl containing 1-6 carbon atoms such as methyl, ethyl, propyl, butyl, amyl, hexyl and the like and all of their isomers.

In the above definition of the general formula, the term of C1~C6 alkoxy c refers to alkyl mentioned above which contains oxygen atom, such as methoxy, ethoxy, propoxy, butoxy, pentoxy, hexyloxy and the like and all of their isomers.

In the above definition of the general formula, the term of C1~C6 alkylthio groups refers to alkoxyl mentioned above in which oxygen atom is replaced by sulfur atom, such as methylthio, ethylthio, propylthio, butylthio, amylthio, hexylthio and the like and all their isomers.

In the above definition of the general formula, the term of C1~C6 alkyl amino groups refers to amino group containing one or two alkyls as defined above such as methylamino, ethylamino, dimethylamino, butylamino, amylamino, hexylamino and the like and all their isomers.

In the above definition of the general formula, the term of halogen refers to fluorine, chlorine, bromine or iodine.

Compounds of the general formula (I) are prepared by the following method:

TMZ was mixed with concentrated sulfuric acid with agitation. Sodium nitrite was dissolved in water and then dropped into aforementioned mixture on an ice bath at temperature of below 15° C. to stir at room temperature overnight. The resulting mixture continued to be added with ice and cool for 1 hour in ice-bath. The solid product of TMZ acid was colleted by filtration, and dried in vacuo.

The mixture of anhydrous DMF and THF was injected into a flask filled with TMZ acid and Pybrop, to stir to let the solid fully dissolved, into which, under the condition of ice bath, DMAP was added. Then, an appropriate amount of anhydrous hydrocarbon alcohol or mercaptan was injected into the resulting mixture to continue to react for half an hour, and stirred at room temperature overnight. After the reaction was completed, the suspension was filtrated by Buchner's funnel. The obtained mother liquor was distilled; the residue was added with ice and extracted by ethyl acetate (10 ml×3). The ethyl acetate phase was combined and dried by anhydrous magnesium sulfate. Ethyl acetate was eliminated by rotating-evaporation to obtain the residues. The residues were sequentially purified with silica gel column and the final product was given after evaporating solvents.

The product was identified by means of IR spectrum, $^1$H-NMR, $^{13}$C-NMR and MS.

According to a further aspect of the invention, the compositions containing said 3,4-dihydro-3-methyl-4-oxoimidazo[5,1-d]-1,2,3,5-tetrazine-8-carboxylate derivatives and the methods for preparing them are provided.

The pharmaceutical compositions of the invention have the activities of anti-tumor, wherein said compositions comprise therapeutically effective amount of one or more compounds of the general formula (I) as the active ingredients together with the conventional pharmaceutically acceptable carriers. Said pharmaceutically acceptable carriers are the ones known in prior art such as liquid or solid excipients, diluents, wetting agents, preservatives, taste-masking agents and coloring agents etc.

The compositions of the invention comprise one or more compounds of said general formula (I) as the active ingredient (s). The preferred compounds of the general formula (I) are selected from a group consisting of:

Methyl 3,4-dihydro-3-methyl-4-oxoimidazo[5,1-d]-1,2,3,5-tetrazine-8-carboxylate,
Ethyl 3,4-dihydro-3-methyl-4-oxoimidazo[5,1-d]-1,2,3,5-tetrazine-8-carboxylate,
Propyl 3,4-dihydro-3-methyl-4-oxoimidazo[5,1-d]-1,2,3,5-tetrazine-8-carboxylate,
Butyl 3,4-dihydro-3-methyl-4-oxoimidazo[5,1-d]-1,2,3,5-tetrazine-8-carboxylate,
1-methyl-butyl 3,4-dihydro-3-methyl-4-oxoimidazo[5,1-d]-1,2,3,5-tetrazine-8-carboxylate,
1-ethyl-butyl 3,4-dihydro-3-methyl-4-oxoimidazo[5,1-d]-1,2,3,5-tetrazine-8-carboxylate,
1-ethyl-propyl 3,4-dihydro-3-methyl-4-oxoimidazo[5,1-d]-1,2,3,5-tetrazine-8-carboxylate,
1-ethyl-amyl 3,4-dihydro-3-methyl-4-oxoimidazo[5,1-d]-1,2,3,5-tetrazine-8-carboxylate,
1-methyl-hexyl 3,4-dihydro-3-methyl-4-oxoimidazo[5,1-d]-1,2,3,5-tetrazine-8-carboxylate,
2-methyl-hexyl 3,4-dihydro-3-methyl-4-oxoimidazo[5,1-d]-1,2,3,5-tetrazine-8-carboxylate,
3-methyl-hexyl 3,4-dihydro-3-methyl-4-oxoimidazo[5,1-d]-1,2,3,5-tetrazine-8-carboxylate,
4-methyl-hexyl 3,4-dihydro-3-methyl-4-oxoimidazo[5,1-d]-1,2,3,5-tetrazine-8-carboxylate,
5-methyl-hexyl 3,4-dihydro-3-methyl-4-oxoimidazo[5,1-d]-1,2,3,5-tetrazine-8-carboxylate,
1-methyl-heptyl 3,4-dihydro-3-methyl-4-oxoimidazo[5,1-d]-1,2,3,5-tetrazine-8-carboxylate,
2-methyl-heptyl 3,4-dihydro-3-methyl-4-oxoimidazo[5,1-d]-1,2,3,5-tetrazine-8-carboxylate,
3-methyl-heptyl 3,4-dihydro-3-methyl-4-oxoimidazo[5,1-d]-1,2,3,5-tetrazine-8-carboxylate,
4-methyl-heptyl 3,4-dihydro-3-methyl-4-oxoimidazo[5,1-d]-1,2,3,5-tetrazine-8-carboxylate,
5-methyl-heptyl 3,4-dihydro-3-methyl-4-oxoimidazo[5,1-d]-1,2,3,5-tetrazine-8-carboxylate,
6-methyl-heptyl 3,4-dihydro-3-methyl-4-oxoimidazo[5,1-d]-1,2,3,5-tetrazine-8-carboxylate,
Amyl 3,4-dihydro-3-methyl-4-oxoimidazo[5,1-d]-1,2,3,5-tetrazine-8-carboxylate,
n-hexyl 3,4-dihydro-3-methyl-4-oxoimidazo[5,1-d]-1,2,3,5-tetrazine-8-carboxylate,
Iso-hexyl 3,4-dihydro-3-methyl-4-oxoimidazo[5,1-d]-1,2,3,5- etrazine-8-carboxylate,
Cyclohexyl 3,4-dihydro-3-methyl-4-oxoimidazo[5,1-d]-1,2,3,5- etrazine-8-carboxylate,
Heptyl 3,4-dihydro-3-methyl-4-oxoimidazo[5,1-d]-1,2,3,5- etrazine-8-carboxylate, and
Octyl 3,4-dihydro-3-methyl-4-oxoimidazo[5,1-d]-1,2,3,5 tetrazine-8-carboxylate.

The more preferred compounds are n-hexyl 3,4-dihydro-3-methyl-4-oxoimidazo[5,1-d]-1,2,3,5-tetrazine-8-carboxylate, iso-hexyl 3,4-dihydro-3-methyl-4-oxoimidazo[5,1-d]-1,2,3,5-tetrazine-8-carboxylate and cyclohexyl 3,4-dihydro-3-methyl-4-oxoimidazo[5,1-d]-1,2,3,5-tetrazine-8-carboxylate; The most preferred compound is n-hexyl 3,4-dihydro-3-methyl-4-oxoimidazo[5,1-d]-1,2,3,5-tetrazine-8-carboxylate.

Further, the compositions of the invention may still comprise pharmaceutically acceptable acidic components, for example the acidic excipients or carriers used in pharmaceutical industry such as oleic acid, stearic acid, linolenic acid, fumaric acid, benzoic acid, tartaric acid, sorbic acid, lactic acid, citric acid, acetic acid, EDTA etc. Those acidic substances play a role of stabilizer to the compounds of the general formula (I).

Also, the inventors of the invention found that the solubility and the carried amount of TMZ-8-carboxylate, the active ingredient of the compositions, will be enhanced in medium by addition of 0.5~20 wt %, preferably 1~10 wt % of pharmaceutically acceptable secondary alcohol or tertiary alcohol, base on the total weight of composition. Wherein, the preferred alcohol is C3~C8 secondary alcohol or tertiary alcohol such as isopropanol, isobutyl alcohol, isoamyl alcohol, tert-butyl alcohol, or their ester derivatives or ether derivatives such as triglyceride and polyglycol ether. Meanwhile, said substances can be used as the solubilizer for the composition and diverse type of formulations comprising TMZ-8-carboxylate derivatives or other imidazo[5,1-d]-1,2,3,5-tetrazin-4-ones.

The composition of the invention may be prepared into any of pharmaceutically conventional formulations. Concretely, the formulations are designed on the basis of the factors below: the desired effect, properties of active ingredients, dosage, the age, sex and the state of illness of patients. These formulations include those suitable for administration, including oral, injection, rectal, topical administration, for example tablet, pill, dispersed powder, capsule, granule, emulsion, solution, suspension, syrup, solid suppository for vaginal or rectal administration, and topical-used patch. The preferred one is topically administered transdermal formulation or orally administered formulation. The most preferred is topically administered transdermal formulation.

The composition and all their formulations of the invention can be prepared by any of methods well known in art of pharmacy.

According to the invention, one of preparation forms suitable for the 3,4-dihydro-3-methyl-4-oxoimidazo[5,1-d]-1,2,3,5-tetrazine-8-carboxylate derivatives is oral preparation, including solid and liquid preparation, of which the suitable orally-administrated solid preparations include tablet, pill, dispersed powder, capsule and granule etc. During the process of preparing solid formulations, bio-agent, TMZ-8-carboxylate derivatives may be either mixed with nothing, or mixed with at least one of inert diluents including the calcium carbonate, starch, alginic acid or lactose etc., and the acidic substances such as fumaric acid, tartaric acid, sorbic acid and citric acid etc. may be added into the formulations. In addition to the components described above, other components may be included in the formulations such as lubricant, magnesium stearate. Besides, the TMZ-8-carboxylate derivatives may be prepared into orally administered liquid preparation forms, including emulsion, solution, suspension and syrup etc. In above liquid preparations always there is aqueous liquid comprising surfactant or liquid paraffin as the inert diluents. Aside from the inert diluents, other additives can also be included, for example wetting-agents, suspending agent such as polyvinylpyrrolidone (PVP), sweetening-agents, taste-masking agents, flavors and preservatives.

Other pharmaceutical formulation form suitable for administrating 3,4-dihydro-3-methyl-4-oxoimidazo[5,1-d]-1,2,3,5-tetrazine-8-carboxylate derivatives is suppository, including solid suppository for vaginal and rectal administration. Aside from those conventional excipient, in order to achieve the purpose of sustained and controlled release, said suppository generally includes biodegradable polymer such as polylactic acid (PLGA), polyanhydride and poly(mixed anhydride) of CPP and SA.

In view of the good properties of the 3,4-dihydro-3-methyl-4-oxoimidazo[5,1-d]-1,2,3,5-tetrazine-8-carboxylate derivatives capable of penetrating skin, the most preferred formulations for them are topically administered transdermal formulation, including tincture, suspension, emulsion, ointment, gel, suppository, film and patch etc. As a rule, the topically administered transdermal formulations generally comprise excipients such as the oil medium, surfactant and the like.

Said oil medium used in the topically administered transdermal formulations is selected from a group consisting of oleic acid, isopropyl myristate (IPM), lauric acid, beeswax, cetyl alcohol, stearyl alcohol, liquid paraffin, vaseline, anhydrous lanolin, stearic acid, cottonseed oil, castor oil, linolenic acid and triglyceride etc. Said common used surfactant is selected from a group consisting of the phospholipid, Myrj type, Brij type, Tween type, acacia, tragacanth, glutin, and vitamin E TPGS (VE TPGS) etc.

The preferred topically administered transdermal patches for the TMZ-8-carboxylate are classified into two groups: matrix type and reservoir type. The matrix type can be classified into the single matrix (AM) and poly matrix (PM). And the reservoir type includes the liquid reservoir system (LRS) and solid reservoir system (SRS), which is composed of multi-layer adhesive (MLA) and multi-layer polymer matrix (MLM). Basically, both matrix and reservoir type of topically administered transdermal formulations of TMZ-8-carboxylates substantially comprising: matrix, polymer materials, drug reservoir (namely drug solution or suspension), rate-moderated membrane, pressure-sensitive adhesives (PSAs) and release layer for protecting PSAs. Further discussion is given as follows:

Solid reservoir type patch: the matrix is the transparent and stable microemulsion and their formulation forms, formed by water phase, oil phase and surfactants at different ratio, which is classified into the liquid and solid type reservoir patch. Said solid type reservoir patch may select either oleic acid or isopropyl myristate (IPM) as the oil phase, lauric acid, beeswax, cetyl alcohol, stearyl alcohol, liquid paraffin, vaseline, anhydrous lanolin, stearic acid, cottonseed oil, castor oil and linolenic acid is also selected as the oil phase.

The preferred oil phase of the TMZ-8-carboxylate solid reservoir patch of the invention is the isopropyl myristate (IPM) or oleic acid, the preferred water phase is water, and the preferred surfactant is VE TPGS and citric acid.

The liquid reservoir type controlled-release patch is made by heat melting non-permeable matrix (or called matrix), liquid drug, rate-moderated membrane, PSAs and release layer.

The structure of each part of the TMZ-8-carboxylate liquid reservoir type patch of the invention is given as follows:

Matrix, i.e. the non-permeable matrix, generally may be those synthesized polymer materials having permeability or non-permeability such as polyester, polyethylene, polyvinyl chloride (PVC), poly(vinylidene chloride) (PVDC) and polyurethane, etc., and natural polymer materials such as cotton and wool etc. The matrix of the invention can be selected from a group consisting of PVC, nitroglycerin(Transdermal®), polydimethylsiloxane (Nitrodisc®), PVP, polyvinyl alcohol (Nitro-Dur® I), complex of polyethene oxide, PEG, all of the PEG derivatives such as polyethylene glycol monomethyl ether or polyethylene glycol dimethyl ether, polyethylene glycol succinate(TPGS) and VE TPGS etc. The preferred is polyethylene, polyvinyl chloride, PVDC, polyurethane or cotton.

Preferably, the rate-moderated membrane is the membrane formed by ethylene and vinyl acetate copolymer, or the homogeneous membranes such as membrane of polyurethane and membrane of glycol diacetate. The PSAs is a unique bio-adhesive, preferably polysiloxane pressure-sensitive gum or polyacrylate pressure-sensitive gum.

The reservoir type controlled release patches of the invention can be prepared by a process comprising following steps: weighing an appropriate amount of n-hexyl TMZ-8-carboxylate and pulverizing it into fine powders; adding water phase such as water, oil phase such as oleic acid etc., and surfactant such as VE TPGS etc.; to blend them well; into which to add pulverized drug, to grind the mixture into microemulsion; following by adding rate-moderated membrane such as the membrane formed by copolymer of ethylene and vinyl acetate and an appropriate amount of PSAs, to stir well, degassing by heat preservation using water bath and spreading them on a polyethylene matrix, drying, and cutting to little pieces to obtain object product.

Said single adhesive matrix patches of the invention are prepared by a process comprising the following steps: dispersing the drug into PSAs by which to control release of the drug. The features of the controlled release system are: the thinner volume, simpler technical process and easier for industrialization. The auxiliaries of drug adhesive matrix of the invention composition are elected from a group consisting of natural or synthetic polymers, including polyvinyl chloride, polyacrylate, polydimethylsiloxane and hydrophilic polymers such as PVP, polyvinyl alcohol, water gel made of gel (e.g.Prostep®), complex of PVP and polyethene oxide, PEG and its derivatives such as polyethylene glycol monomethyl ether or polyethylene glycol dimethyl ether, polyethylene glycol succinate and VE TPGS; The preferred is polyacrylate.

Usually, said TMZ-8-carboxylate is administrated at a dosage of 0.1~200 mg/kg body weight/day, preferably, 1~20 mg/kg body weight/day.

Study of Lipid Solubility, Stability and Solubility for TMZ-8-carboxylate

The studies showed that, compared with TMZ, the lipid solubility of TMZ-8-carboxylate derivatives have been significantly improved. For example, taking Log P as standard, Log P for TMZ is −0.66, while Log P for n-hexyl TMZ-8-carboxylate is 2.56. It means that n-hexyl TMZ-8-carboxylate is an ideal drug for topically transdermal administration (As the method for measuring Log P, See Leo and Hansch, Chemical Reviews 71 No. 6, December 1971 (Partition Coefficients and Their Uses, Leo A., Hansch C. and Elkins D.).

The inventors of the invention found that the stability would be enhanced greatly for the TMZ-8-carboxylate derivatives alone or together with other imidazo[5,1-d]-1,2,3,5-tetrazin-4-ones under acidified conditions (pH 1~6.5) obtained by adding pharmaceutically acceptable acidic components. So, the stability of active ingredients would significantly enhance when the TMZ-8-carboxylate derivatives was used as active ingredients in the liquid formulation such as tincture, suspension, emulsion and injection, and solid formulations such as ointment, suppository and film. Said acidic substances include oleic acid, stearic acid, linolenic acid, fumaric acid, benzoic acid, tartaric acid, sorbic acid, lactic acid, citric acid, acetic acid, EDTA and the like.

meanwhile, the inventors of the invention also found that the solubility and the carried amount of TMZ-8-carboxylate, the active ingredient in the composition, will be enhanced in medium by addition of 0.5%~20% of pharmaceutically acceptable secondary alcohol or tertiary alcohol such as isopropanol, isobutyl alcohol, isoamyl alcohol, tert-butyl alcohol, or their ester or ether derivatives such as triglyceride, polyglycol ether. Accordingly, secondary alcohol or tertiary alcohol such as isopropanol, isobutyl alcohol, isoamyl alcohol, tert-butyl alcohol etc. can be used as the solubilizer in the composition comprising TMZ-8-carboxylate derivatives and other imidazo[5,1-d]-1,2,3,5-tetrazin-4-one.

Based on the findings, the invention provides an anti-tumor composition, which comprises one or more TMZ-8-carboxylate derivatives, pharmaceutically acceptable acidic substances, optionally pharmaceutically acceptable secondary alcohol or tertiary alcohol and their derivatives, and pharmaceutically acceptable excipients and/or carriers. The invention also provides diverse preparation made by the composition of the invention.

Following experiments of in vitro pharmaceutical actions against carcinoma for methyl TMZ-8-carboxylate, butyl TMZ-8-carboxylate and n-hexyl TMZ-8-carboxylate will be given to illustrate their beneficial efficacy.

In Vitro Study of TMZ-8-carboxylate on Effect in Killing Tumor Cell

The experiment was carried out for methyl TMZ-8-carboxylate, butyl TMZ-8-carboxylate, n-hexyl TMZ-8-carboxylate, and TMZ acid which had been known as an active compound against carcinoma, and used fluorouracil injection (10 ml:0.25 g, purchased from Xudong Pharmaceutical Co. Ltd, the batch number was 000612) as the drug for the positive control. Cancer cell strains used in experiments included HCT-8(human colon carcinoma cells), A549 (human lung carcinoma cells), MCF-7(human breast carcinoma cells), Bel7402 (human liver carcinoma cells), BGC-823(human gastric carcinoma cells) and MV3 (human melanoma cells).

Drugs & Reagents

TMZ acid is white powder; Methyl TMZ-8-carboxylate, butyl TMZ-8-carboxylate and n-hexyl TMZ-8-carboxylate, white scaly crystals, manufactured by the method described in Example 2; Fluorouracil injection (10 ml: 0.25 g): as drug for the positive control, manufactured by Xudong Pharmaceutical Co. Ltd, the batch number 000612; RPMI: produced by GIBCO; Calf serum: manufactured by Sijiqing bio-engineer material Co. Ltd, Hangzhou; and MTT: produced by Bebco.

Cell Strains

All cancer cell strains of HCT-8, A549, MCF-7, Bel-7402, BGC-823, MV3 and B16 was fostered and transferred of culture by Institute of Materia Medica, Chinese Academy of Medical Sciences and Peking Union Medical College.

Apparatus: BIORAD 550 Enzyme Labeling Instrument.

Method:

Tetrazolium salt [3-(4,5-dimethylthiazol-2-yl)-2,5-diphenyl- tetrazolium bromide, MTT] reduction assay was used. All the well-grown carcinoma cells were collected, prepared intol $1\times10^4$/ml cell suspension with the RPMI 1640 culture solution containing 10% calf serum, and inoculated in 96-well culture plate, with 100 uL per well (containing 1000 cancer cells). After 24 hours of culture in 5% $CO_2$ thermos incubator at temperature of 37° C. the drugs were added. Blank control group was established and the drug for the positive control was Fluorouracil. The tested drugs were divided into five groups at different concentrations, each concentration was tested for three times parallelly, and placed in 5% $CO_2$ thermos incubator at temperature of 37° C. to culture for four days. The culture solution was discarded and 100 uL of MTT solution (0.4 mg/ml, prepared with RPMI 1640) was added per well to continue to culture for four hours at temperature of 37° C. The supernate was discarded and 150 uL of DMSO was added to dissolve Fomazan granules. After slight agitation, the OD value was measured with BIORAD 550 enzyme labeling instrument at the measuring wavelength of 540 nm and the reference wavelength of 450 nm.

Results

Data of cell inhibiting rate was then plotted vs. the concentration of drugs to obtain the dose-reaction curve, by which 50% inhibitory concentration $IC_{50}$ was calculated (see Table 1 and Table 2).

The result (see Table 1) showed that the $IC_{50}$ ranges for the selected cell strains of four drugs (methyl TMZ-8-carboxylate, butyl TMZ-8-carboxylate, n-hexyl TMZ-8-carboxylate and TMZ acid) were 10~30 ug/ml, and no significant difference among them in acting on the cells was observed.

TABLE 1

Results for killing tumor cells by MTT method

| | | $IC_{50}$ | | | |
| --- | --- | --- | --- | --- | --- |
| Cell strains | Fluorouracil | TMZ acid | n-hexyl TMZ-8-carboxylate | methyl TMZ-8-carboxylate | butyl TMZ-8-carboxylate |
| MV3 | 0.427 | 14.625 | 8.835 | 8.827 | 7.568 |
| MCF-7 | 0.629 | 14.911 | 19.995 | 17.665 | 16.558 |
| Bel-7402 | 0.495 | 16.957 | 27.203 | 25.304 | 24.368 |
| A549 | 0.126 | >19.5 | 26.632 | 27.001 | 25.336 |

TABLE 1-continued

Results for killing tumor cells by MTT method

| | | | IC$_{50}$ | | |
|---|---|---|---|---|---|
| Cell strains | Fluorouracil | TMZ acid | n-hexyl TMZ-8-carboxylate | methyl TMZ-8-carboxylate | butyl TMZ-8-carboxylate |
| HCT-8 | 0.606 | 18.525 | 28.644 | 28.369 | 27.359 |
| BGC-823 | 0.722 | >19.5 | >19.5 | >19.5 | >19.5 |

Effect of Topical Administration of Hexyl TMZ-8-carboxylate on Growth of Xenotransplanted Human Melanoma in MV3 Nude Mouse Hexyl TMZ-8-carboxylate was selected as the representative to investigate the influence of TMZ-8-carboxylate derivatives on the growth of xenotransplanted human melanoma in MV3 nude mouse.

Hexyl TMZ-8-carboxylate was dissolved in DMSO to obtain 50 mg/ml solution. Human melanoma was xenotransplanted to nude mouse of BALB/c-nu to allow it to grow. Until the tumor expanded to the volume of 100~300 mm$^3$, all animals were divided into two groups in accordance with the size of tumor, eight mice per group.

Of these two groups, one was the treatment group in therapeutical treatment by spreading the solution of hexyl TMZ-8-carboxylate; another was the control group where the tumor grows naturally.

In the treatment group, the drug was administered by spreading drug at the position of tumor and surrounding area (2 cm×2 cm) twice a day (once on Saturday and Sunday). Every time, when the solution was dried, administration was repeated for 1 to 2 times. The daily average dose of hexyl TMZ-8-carboxylate administered for a mouse totally was about 20 mg.

The volume of tumor in mouse was measured twice a week, so as to observe and record their growth dynamically. Until the tumor of the control group grew up to a certain volume, all the mice were killed the tumors were stripped off and weighed, growth inhibition rate was calculated. Tumor proliferation (T/C(%)) was calculated using relative volume of tumor in two groups.

Tumor volume (TV) was calculated by the equation as follows:

Length×width$^2$÷2

The relative tumor volume is calculated by the equation as follows:

$V_t/V_o$

Wherein the $V_o$ is the TV measured at the time when the animals were raised in separate cages, and $V_o$ is the TV measured each time after.

The t-test was used to compare the statistical difference between two groups in many indexes such as tumor weight, TV and RTV. The relative tumor proliferation rate (T/C(%)) was used as the index of bioactivity for anti tumor, which was calculated as follows:

$$T/C(\%) = \frac{\text{Treatment group}(T)\ RTV}{\text{Control group}(C)\ RTV} \times 100$$

Criteria to Evaluate Effects:

The effect was evaluated by statistical analysis. The effect was regarded as invalid when T/C (%) is more than 60, and as effective when T/C (%) is equal to or less than 60 and p<0.05.

The results showed that hexyl TMZ-8-carboxylate had significant inhibiting effects on the growth of carcinomas in the mice, and strong killing effects on carcinoma cells such as human melanoma MV3, 20 mg of which daily externally-administered in a mouse had manifested actions in inhibiting grafted carcinomas. By the end of experiment, comparing with the control group, there were statistically significant difference for both weight and volume of tumor. The results may be seen in FIGS. 1, 2 and Table 2. FIG. 1 shows the effect on growth of human melanomas by spreading hexyl TMZ-8-carboxylate can be seen that the growth of human melanomas in the treatment group has been inhibited markedly compared with the control group (or negative control group). FIG. 2 is the realistic pictures of two group mice. The upper part of the first picture displays a picture of the mice in the control group, and the lower part displays a picture of the mice in the treatment group. The upper part of second picture displays a picture of entity of tumor in control group, and the lower part displays a picture of entity of tumor in the treatment group. Table 2 reveals the influence for tumor growth of the mice bearing MV3 by spreading hexyl TMZ-8-carboxylate.

TABLE 2

Influence by spreading hexyl TMZ-8-carboxylate on the mice bearing MV3 (20 mg/day/mouse)

| Groups | Number of mice(n) | | Body weight(g) | | Tumor volume (mm$^3$) | | RTV | T/C(%) | Weight of tumor (g) | Inhibiting rate (%) |
|---|---|---|---|---|---|---|---|---|---|---|
| | Beginning test | End test | Beginning test | End test | Beginning test | End test | | | | |
| Negative control group | 8 | 8 | 22.6 ± 1.56 | 24.8 ± 0.535 | 106 ± 56.3 | 2456 ± 960.3 | 9.35 ± 7.88 | | 2.15 ± 0.86 | |
| Group of hexyl TMZ-8-carboxylate | 8 | 8 | 24.0 ± 1.48 | 25.6 ± 3.64 | 115 ± 36 | 635 ± 545.1* | 3.25 ± 1.85 | 33.7 | 0.45 ± 0.335 | 83.2 |

Note:
*Compared with the control group, P < 0.05, the body weight, tumor weight and Tumor volume are expressed as X ± SD.

BEST MODES FOR CARRYING OUT THE INVENTION

Figure 1:
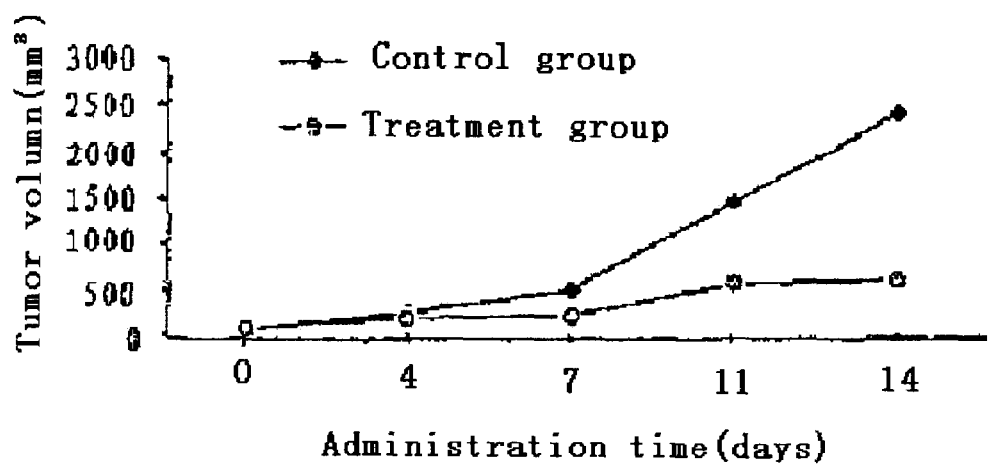
FIG. 1 is the growth curve of tumor, indicating the inhibiting effects of n-hexyl TMZ-8-carboxylate on growth of human melanomas.
Figure 2:
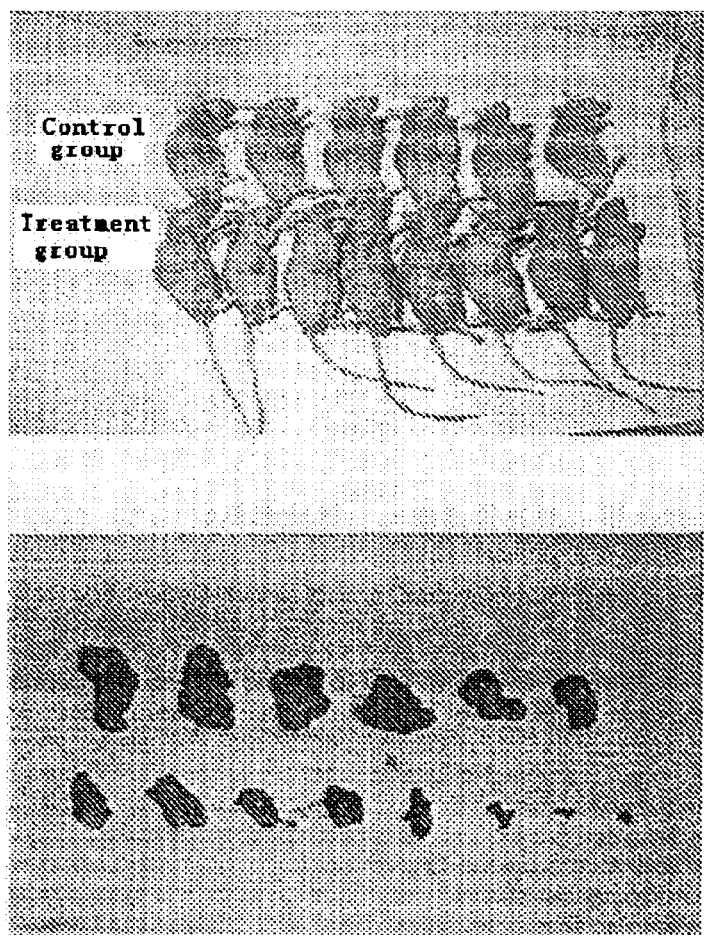
FIG. 2 is the real body picture of mice of both treatment group and control group.

The following examples illustrate the invention without any way limiting its scope.

EXAMPLE 1

Preparation of TMZ Acid (EP0252682)

TMZ (2.577 mmol, 0.5 g) was mixed with concentrated sulfuric acid (4 ml) with agitation. Sodium nitrite (9.4 mmol, 0.65 g) was dissolved in 2.6 ml of water and then dropped into aforementioned mixture on an ice bath at temperature of below 15° C. to stir at room temperature overnight. The resulting mixture continued to be added with log of ice and cool for 1 hour in ice-bath. The solid product was colleted by filtration, and dried in vacuo to give 0.493 g of TMZ acid. The yield was 98.6%.

EXAMPLE 2

Preparation of TMZ-8-Carboxylate

The mixture of anhydrous DMF (2 ml) and THF (3 ml) was injected into a flask filled with TMZ acid (1 mmol, 0.195 g) prepared in accordance of Example 1 and Pybrop (1 mmol, 0.466 g), to stir to let the solid fully dissolved, into which, under the condition of ice bath, DMAP (2 mmol, 0.244 g) was added. Then, an appropriate amount of anhydrous hydrocarbon alcohol or mercaptan (2.2 mmol) was injected into the resulting mixture to continue to react for half an hour, and stirred at room temperature overnight. After the reaction was completed, the suspension was filtrated by Buchner's funnel. The obtained mother liquor was distilled; the residue was added with log of ice and extracted by ethyl acetate (10 ml×3). The ethyl acetate phase was combined and dried by anhydrous magnesium sulfate. Ethyl acetate was eliminated by rotating-evaporation to obtain the residues. The residues were sequentially purified with silica gel column and the final product was given after evaporating solvents.

The product was identified by means of IR spectrum, $^1$H-NMR, $^{13}$C-NMR and MS. The typical data was shown as follows:

1. Methyl TMZ-8-carboxylate $^1$H NMR ($_{d6}$-DMSO/ppm) δ 8.86 (s, 1, H-6), 3.90 (s, 3,C$\underline{H}_3$—O), 3.87 (s, 3, C$\underline{H}_3$—N) $^{13}$C NMR ($_{d6}$-DMSO/ppm) δ 161 ($\underline{C}$OO), 139 (C-4), 137 (C-6), 129 (C-9), 126 (C-8), 52.2 (O$\underline{C}H_2$), 36.4 (N$\underline{C}H_3$) $ν_{max}$ (KBr): 3489, 2961 (C—H), 1752 (C=O), 1727 (C=O), 1214 (C—O), 1062 (C—O), 828, 556 cm$^{-1}$ MS:+ES: m/z=232 [M+H]$^+$, 214[M+H—H$_2$O]$^+$

2. Ethyl TMZ-8-carboxylate $^1$H NMR (CDCl$_3$/ppm) δ 8.45 (s, 1, H-6), 4.52 (q, 2, J=7.1 Hz, C$\underline{H}_2$—O), 4.04 (s, 3, C$\underline{H}_3$—N), 1.45 (t, 3, J=7.1 Hz, CH$_2$-C$\underline{H}_3$) $^{13}$C NMR ($_{d6}$-DMSO/ppm) δ 161 ($\underline{C}$OO), 139 (C-4), 137 (C-6), 129 (C-9), 127 (C-8), 60.9 (O$\underline{C}H_2$), 36.4 (N$\underline{C}H_3$), 14.3 (CH$_2\underline{C}H_3$) $ν_{max}$ (KBr): 3478, 2991 (C—H), 1754 (C=O), 1700 (C=O), 1467 (C—O), 1258 (C—O), 1060 (C—O), 844, 561 cm$^{-1}$ MS:+ES: m/z=246 [M+H]$^+$, 228[M+H—H$_2$O]$^+$

3. Propyl TMZ-8-carboxylate $^1$H NMR (CDCl$_3$/ppm) δ 8.46 (s, 1, H-6), 4.41 (t, 2, J=6.7 Hz, C$\underline{H}_2$—O), 4.03 (s, 3, C$\underline{H}_3$—N), 1.83 (sextet, 2, J=7.1 Hz, C—C$\underline{H}_2$—C), 1.03 (t, 3, J=7.4 Hz, C—C$\underline{H}_3$) $^{13}$C NMR (CDCl$_3$/ppm) δ 160 ($\underline{C}$OO), 138 (C-4), 136 (C-6), 130 (C-9), 128 (C-8), 67.1 (O$\underline{C}H_2$), 36.5 (N$\underline{C}H_3$), 21.7 ($\underline{C}H_2$CH$_3$), 8.87 (CH$_2\underline{C}H_3$) $ν_{max}$ (KBr): 3122, 2960 (C—H), 1729 (C=O), 1700(C=O), 1457 (C—O), 1200 (C—O), 1174 (C—O), 1052, 942 cm$^{-1}$ MS:+ES: m/z=260 [M+H]$^+$, 242[M+H—H$_2$O]$^+$

4. Butyl TMZ-8-carboxylate $^1$H NMR (CDCl$_3$/ppm) δ 8.45 (s, 1 H-6), 4.45 (t, 2, J=7.1 Hz, C$\underline{H}_2$—O), 4.03 (s, 3, C$\underline{H}_3$—N), 1.79 (quintet, 2, J=7.4 Hz, C—C$\underline{H}_2$—C), 1.46 (sextet, 2, J=7.3 Hz, C—C$\underline{H}_2$—CH$_3$), 0.95 (t, 3, J=7.3 Hz, C—C$\underline{H}_3$) $^{13}$C NMR ($_{d6}$-DMSO/ppm) δ 161 ($\underline{C}$OO), 139 (C-4), 137 (C-6), 129 (C-9), 127 (C-8), 64.5 (O$\underline{C}H_2$), 36.4 (N$\underline{C}H_3$), 30.3 (OCH$_2\underline{C}H_2$), 18.7 ($\underline{C}H_2$CH$_3$), 13.6 (CH$_2\underline{C}H_3$) $ν_{max}$ (KBr): 3156, 2967 (C—H), 1746 (C=O), 1467 (C—O), 1261 (C—O), 1054 (C—O), 823, 561 cm$^{-1}$ MS:+ES: m/z=274 [M+H]$^+$, 256[M+H—H$_2$O]$^+$

5. Amyl TMZ-8-carboxylate $^1$H NMR (CDCl$_3$/ppm) δ 8.46 (s, 1, H-6), 4.45 (t, 2, J=7.0 Hz, C$\underline{H}_2$—O), 4.03 (s, 3, C$\underline{H}_3$—N), 1.79 (quintet, 2, J=7.1 Hz, C—C$\underline{H}_2$—C), 1.29-1.40 (m, 4, C—(C$\underline{H}_2$)$_2$—CH$_3$), 0.96 (t, 3, J=6.9 Hz, C—C$\underline{H}_3$) $^{13}$CMR ($_{d6}$-DMSO/ppm) δ 161 ($\underline{C}$OO), 139 (C-4), 137 (C-6), 129 (C-9), 127 (C-8), 64.6 (O$\underline{C}H_2$), 36.4 (N$\underline{C}H_3$), 30.9 (OCH$_2\underline{C}H_2$), 28.2 (O(CH$_2$)$_2\underline{C}H_2$), 22.8 ($\underline{C}H_2$CH$_3$), 14.0 (CH$_2\underline{C}H_3$) $ν_{max}$ (KBr): 3136, 2967 (C—H), 1736 (C=O), 1459 (C—O), 1231 (C—O), 1154 (C—O), 923, 761 cm$^{-1}$ MS:+ES: m/z=288 [M+H]$^+$, 270[M+H—H$_2$O]$^+$

6. Hexyl TMZ-8-carboxylate $^1$H NMR (CDCl$_3$/ppm) δ 8.49 (s, 1, H-6), 4.45 (t, 2, J=6.9 Hz, C$\underline{H}_2$—O), 4.04 (s, 3, C$\underline{H}_3$—N), 1.79 (quintet, 2, J=7.1 Hz, C—C$\underline{H}_2$—C), 1.29-1.40 (m, 6, C—(C$\underline{H}_2$)$_3$—CH$_3$), 0.87 (t, 3, J=6.9 Hz, C—C$\underline{H}_3$) $^{13}$CMR ($_{d6}$-DMSO/ppm) δ 161 ($\underline{C}$OO), 139 (C-4), 137 (C-6), 129 (C-9), 127 (C-8), 64.8 (O$\underline{C}H_2$), 36.4 (N$\underline{C}H_3$), 30.9 (OCH$_2\underline{C}H_2$), 28.2 (O(CH$_2$)$_2\underline{C}H_2$), 25.1 ($\underline{C}H_2$CH$_2$CH$_3$), 22.1 ($\underline{C}H_2$CH$_3$), 13.9 (CH$_2\underline{C}H_3$) $ν_{max}$ (KBr): 3156, 2967 (C—H), 1746 (C=O), 1467 (C—O), 1261 (C—O), 1054 (C—O), 823, 561 cm$^{-1}$ MS:+ES: m/z=302 [M+H]$^+$, 284[M+H—H$_2$O]$^+$

7. Heptyl TMZ-8-carboxylate $^1$H NMR (CDCl$_3$/ppm) δ 8.39 (s, 1, H-6), 4.38 (s, 2, C$\underline{H}_2$—O), 4.00 (s, 3, C$\underline{H}_3$—N), 1.75 (s, 2, C—C$\underline{H}_2$—C), 1.19 (s, 8, C—(C$\underline{H}_2$)$_4$—C), 0.83 (s, 3, C—C$\underline{H}_3$) $^{13}$C NMR ($_{d6}$-DMSO/ppm) δ 161 ($\underline{C}$OO), 139 (C-4), 137 (C-6), 129 (C-9), 127 (C-8), 64.8 (OCH$_2$), 36.4 (NCH$_3$), 31.1 (OCH$_2$CH$_2$), 2×28.4 (OCH$_2$CH$_2$(CH$_2$)$_2$), 25.3 (CH$_2$CH$_2$CH$_3$), 22.1 (CH$_2$CH$_3$), 13.8 (CH$_2$CH$_3$) $v_{max}$ (KBr): 3146, 2927 (C—H), 2858 (C—H), 1748 (C=O), 1718 (C=O), 1457 (C—O), 1245 (C—O), 828, 566 cm$^{-1}$ MS:+ES: m/z=316 [M+H]$^+$, 398[M+H—H$_2$O]$^+$ 8. Octyl TMZ-8-carboxylate $^1$H NMR (CDCl$_3$/ppm) δ 8.36 (s, 1, H-6), 4.36 (s, 2, CH$_2$—O), 3.95 (s, 3, CH$_3$—N), 1.74 (s, 2, C—CH$_2$—C), 1.19 (s, 10, C—(CH$_2$)$_5$—C), 0.78 (s, 3, C—CH$_3$) $^{13}$C NMR ($_{d6}$-DMSO/ppm) δ 160 (COO), 139 (C-4), 137 (C-6), 129 (C-9), 127 (C-8), 64.8 (OCH$_2$), 36.4 (NCH$_3$), 31.2 (OCH$_2$CH$_2$), 2×28.6 (OCH$_2$CH$_2$(CH$_2$)$_2$), 28.2 (O(CH$_2$)$_4$CH$_2$), 25.4 (CH$_2$CH$_2$CH$_3$), 22.1 (CH$_2$CH$_3$), 13.9 (CH$_2$CH$_3$) $v_{max}$ (KBr): 2925, 2853, 1758, 1720, 1467, 1255, 838, 556 cm$^{-1}$ MS:+ES: m/z=330 [M+H]$^+$, 312[M+H—H$_2$O]$^+$

EXAMPLE 3

Figure 3:
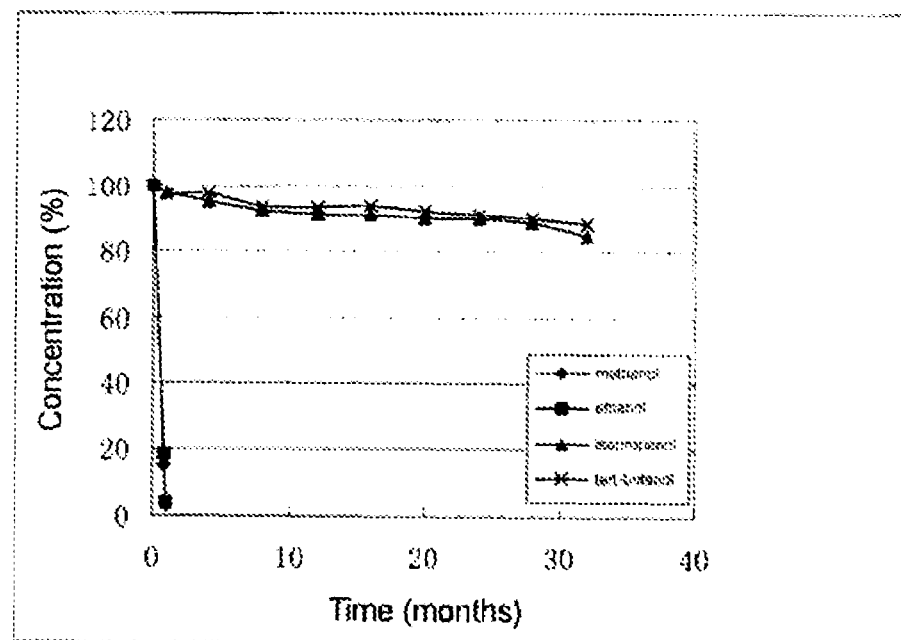
FIG. 3 shows the results of stability of n-hexyl TMZ-8-carboxylate in the common alcohols.

Study of Stability of TMZ-8-carboxylate Derivatives in Alcohols n-hexyl TMZ-8-carboxylate was weighed accurately and prepared into 1% of solution by diluting respectively with methanol, ethanol, isopropanol and tert-butyl alcohol. Three sample solutions (20 ml) were taken out in each of above solutions and placed into 50 ml volumetric brown glass bottle, sealed and allowed to stand at room temperature. At time of 1, 4, 8, 12, 16, 20, 24, 28, 32 months after beginning, the solutions were sampled and determined the concentration of n-hexyl TMZ-8-carboxylate by HPLC, to calculate the average value of three parallel solutions and plotted. The results revealed that n-hexyl TMZ-8-carboxylate rapidly decomposes in the methanol and ethanol, while keeps stable in the isopropanol and tert-butyl alcohol. See FIG. 3.

EXAMPLE 4

Study of the Stability of TMZ-8-carboxylate in Acidic Medium

Figure 4:
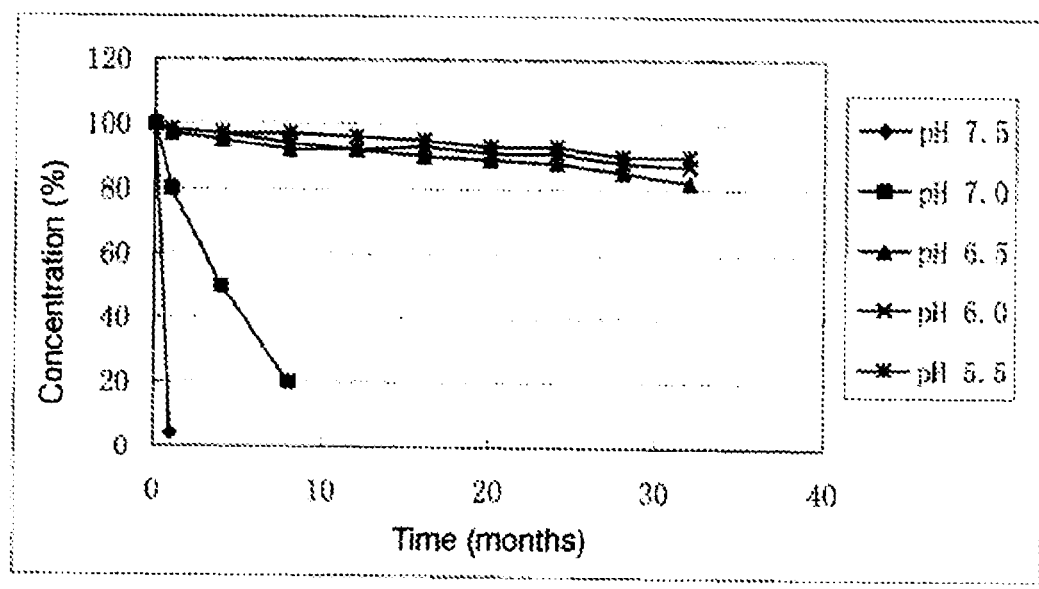
FIG. 4 shows the influence of the pH value of medium to the stability of n-hexyl TMZ-8-carboxylate.

The sodium hydroxide and citric acid were accurately weighed and respectively diluted with water to form the solution with the pH value of 7.5, 7.0, 6.5, 6.0 and 5.5. n-Hexyl TMZ-8-carboxylate was accurately weighed, and dissolved into said aqueous solutions with different pH values to form a series of 1% solutions of n-hexyl TMZ-8-carboxylate. Three sample solutions (20 ml) were taken out in each of above solutions and placed into 50 ml volumetric brown glass bottle, sealed and allowed to stand at room temperature. At 1, 4, 8, 12, 16, 20, 24, 28, 32 months after beginning, the solutions were sampled and determined the concentration of n-hexyl TMZ-8-carboxylate by HPLC, to calculate the average of three parallel solutions and plotted. The results revealed that n-hexyl TMZ-8-carboxylate rapidly decomposes under the weakly alkaline (pH7.5) or neutral (pH7.0) medium, while keep relatively stable in the acidic (pH<7.0) medium. See FIG. 4.

EXAMPLE 5

Preparation of Solid Reservoir Type System of Methyl TMZ-8-carboxylate 3 g of methyl TMZ-8-carboxylate was weighed, pulverized into fine powder, and mixed with 20 g of water, 50 g of oleic acid, 30 g of VE TPGS and an appropriate amount of citric acid to form the microemulsion by grinding. An appropriate amount of rate-moderated membrane (copolymer of ethylene and vinyl acetate) and PSAs (polysiloxane pressure-sensitive gum) were added. The resulting mixture was stirred well, degassed by heat preservation using water bath, and spread on a polythene matrix. Dried and cut to 50 patches to obtain object product.

EXAMPLE 6

Preparation of Solid Reservoir Type System of Propyl TMZ-8-carboxylate

The preparing method hereof referred to Example 5 to prepare 50 pieces of patches, wherein methyl TMZ-8-carboxylate was replaced by propyl TMZ-8-carboxylate as the active ingredient.

EXAMPLE 7

Preparation of Solid Reservoir Type System of Butyl TMZ-8-carboxylate

The preparing method hereof referred to Example 5 to prepare 50 pieces of patches, wherein methyl TMZ-8-carboxylate was replaced by butyl TMZ-8-carboxylate as the active ingredient.

EXAMPLE 8

Preparation of Solid Reservoir Type System of Heptyl TMZ-8-carboxylate

The preparing method hereof referred to Example 5 to prepare 50 pieces of patches, wherein methyl TMZ-8-carboxylate was replaced by heptyl TMZ-8-carboxylate as the active ingredient.

EXAMPLE 9

Preparation of Solid Reservoir Type System of n-hexyl TMZ-8-carboxylate

The preparing method hereof referred to Example 5 to prepare 50 pieces of patches, wherein methyl TMZ-8-carboxylate was replaced by n-hexyl TMZ-8-carboxylateas the active ingredient.

EXAMPLE 10

Preparation of Solid Reservoir Type System of Ethyl TMZ-8-carboxylate

The preparing method hereof referred to Example 5 to prepare 50 pieces of patches, wherein methyl TMZ-8-carboxylate was replaced by ethyl TMZ-8-carboxylate as the active ingredient.

EXAMPLE 11

Preparation of Patch of Amyl TMZ-8-carboxylate

The preparing method hereof referred to Example 5 to prepare 50 pieces of patches, wherein methyl TMZ-8-carboxylate was replaced by amyl TMZ-8-carboxylate as the active ingredient.

EXAMPLE 12

Preparation of Capsule of Butyl TMZ-8-carboxylate 5 mg of Butyl TMZ-8-carboxylate was grinded into fine powder and filled in hard glutin capsule to prepare the capsule.

EXAMPLE 13

Preparation of Ccapsule of Heptyl TMZ-8-carboxylate 10 mg of heptyl TMZ-8-carboxylate was grinded into fine powder and filled in hard glutin capsule to make the capsule.

EXAMPLE 14

Preparation of Capsule of Octyl TMZ-8-carboxylate 10 mg of octyl TMZ-8-carboxylate was grinded into fine powder and filled in hard glutin capsule to make the capsule.

EXAMPLE 15

Preparation of Capsule of n-hexyl TMZ-8-carboxylate

Formulation

| | |
|---|---|
| n-hexyl TMZ-8-carboxylate | 10 mg |
| Lactose | 65 mg |
| Pregelatinized starch | 25 mg |
| sodium croscarmellose | 3 mg |
| Colloidal silicon dioxide | 0.25 mg |
| Magnesium stearate | 0.30 mg | n-Hexyl TMZ-8-carboxylate, lactose, pregelatinized starch, sodium croscarmellose(sodium crosslinked carboxymethyl cellulose) were respectively passed through 65-mesh screen for later use. n-Hexyl TMZ-8-carboxylate was weighed according to the amount as described in the formulation and mixed with other auxiliaries in a manner of increasing the amounts proportionally. The mixture was passed through 65-mesh screen for three times. The angle of repose was measured as less than 30°. After content tested and capacity determined, capsules were prepared by loading the mixture into No. 3 capsules.

EXAMPLE 16

Preparation of Capsule of Octyl TMZ-8-carboxylate

Formulation

| | |
|---|---|
| Octyl TMZ-8-carboxylate | 10 mg |
| Lactose | 65 mg |
| Pregelatinized starch | 25 mg |
| Sodium croscarmellose | 3 mg |
| Colloidal silicon dioxide | 0.25 mg |
| Magnesium stearate | 0.30 mg |

The preparing method referred to Example 14, wherein n-hexyl TMZ-8-carboxylate was replaced by octyl TMZ-8-carboxylate as the active ingredient. The desired capsule was obtained.

EXAMPLE 17

Preparation of Capsule of 3-methyl-heptyl TMZ-8-carboxylate

Formulation

| | |
|---|---|
| 3-Methyl-heptyl TMZ-8-carboxylate | 10 mg |
| Lactose | 65 mg |
| Pregelatinized starch | 25 mg |
| Sodium croscarmellose | 3 mg |
| Colloidal silicon dioxide | 0.25 mg |
| Magnesium stearate | 0.30 mg |

The preparing method referred to Example 14, wherein n-hexyl TMZ-8-carboxylate was replaced by 3-methyl-heptyl TMZ-8-carboxylate as the active ingredient. The desired capsule was obtained.

EXAMPLE 18

Preparation of Patch of 2-ethyl-amyl TMZ-8-carboxylate

Formulation

| | |
|---|---|
| 2-ethyl-amyl TMZ-8-carboxylate | 3 g |
| Water | 20 g |
| Oleic acid | 50 g |
| VE TPGS | 30 g |
| Citric acid | appropriate amount |

Above substances were mixed well to make into microemulsion, into which an appropriate amount of rate-moderated membrane (copolymer of ethylene and vinyl acetate) and PSAs (polysiloxane pressure-sensitive gum) were added. The resulting mixture was stirred well, degassed by heat preservation using water bath, and spread on a polythene matrix. Dried and cut to 50 patches to obtain the object product.

EXAMPLE 19

Preparation of Topically-Administered Transdermal Emulsion of n-hexyl TMZ-8-carboxoylate 3 g of n-hexyl TMZ-8-carboxoylate was pulverized into fine powder and mixed with 20 g of water, 50 g of oleic acid, 30 g of phospholipid, an appropriate amount of citric acid or sorbic acid (pH5.5), vitamin E and isopropanol to make into microemulsion. It could either be used directly, or be divided into 50 portions and made to 25 patches.

EXAMPLE 20

Preparation of Topically Administered Transdermal Emulsion of n-hexyl TMZ-8-carboxoylate 3 g of n-Hexyl TMZ-8-carboxoylate was pulverized into fine powder and mixed with 20 g of water, 35 g of VE TPGS, 45 g of long or moderate chain triglyceride, an appropriate amount of lactic acid or benzoic acid (pH5.0) and isopropanol to make into microemulsion. It could either be used directly, or be divided into 50 portions and made to 25 patches.

EXAMPLE 21

Preparation of Topically Administered Transdermal Ointment of n-hexyl TMZ-8-carboxoylate 3 g of n-Hexyl TMZ-8-carboxoylate was pulverized into fine powder and mixed with 15 g of water, 50 g of VE TPGS, 35 g of isopropyl myristate, an appropriate amount of malic acid or fumaric acid (pH 6.0) and isobutyl alcohol to make into ointment. It could either be used directly, or could be made it into microemulsion and divided into 50 portions, then made to 25 patches.

What claimed is:

1. A pharmaceutical composition having activity of anti-tumor comprising a therapeutically effective amount of one or more compounds of formula I as the active ingredient, conventional pharmaceutically acceptable carriers, and one or more pharmaceutically acceptable acidic components, wherein said acidic component is selected from a group consisting of oleic acid, stearic acid, linolenic acid, fumaric acid, benzoic acid, tartaric acid, sorbic acid, lactic acid, citric acid, acetic acid and EDTA,

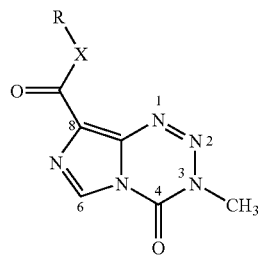

I wherein X is O or S;

R is substituted or unsubstituted C3~C10 straight or branched alkyl, C3~C10 cycloalkyl, C3~C10 straight or branched alkenyl or C3~C10 straight or branched chain alkynyl;

and R has substituent(s), said substituent(s) is C1~C6 alkyl, C1~C6 alkoxy, C1C6 alkylthio group, C1~C6 alkyl amino group, phenyl or phenyl substituted by halogen.

2. The pharmaceutical composition of claim 1, wherein said composition further comprises one or more pharmaceutically acceptable C3~C8 tertiary alcohol or secondary alcohol, or their ester or ether derivatives.

3. The pharmaceutical composition of claim 1, wherein said active ingredient is administered to patients in a dosage of 0.1~200 mg/kg body weight/day.

4. The pharmaceutical composition according to claim 3, wherein said dosage 15 range of the active ingredient is 1~20 mg/kg body weight/day.

5. The pharmaceutical composition according to claim 1, wherein said composition is made into any one of pharmaceutically acceptable preparation forms.

6. The pharmaceutical composition according to claim 5, wherein said composition is made into topically administered transdermal preparation form or orally administered preparation form.

7. The pharmaceutical composition according to claim 6, wherein said topically administered transdermal preparation form is topically transdermal patch.

8. The pharmaceutical composition according to claim 7, wherein said topically transdermal patch is the matrix type controlled-release patch, the solid reservoir type controlled-release patch or liquid reservoir type controlled-release patch.

9. The pharmaceutical composition according to claim 8, wherein said topically transdermal patch is solid reservoir type controlled-release patch, in which the water phase is water and the oil phase is one or more substances selected from a group consisting of following: oleic acid, isopropyl myristate, lauric acid, beeswax, cetyl alcohol, stearyl alcohol, liquid paraffin, vaseline, anhydrous lanolin, stearic acid, cottonseed oil, castor oil and linolenic acid.

10. The pharmaceutical composition according to claim 9, wherein said oil phase is oleic acid or isopropyl myristate.

11. The pharmaceutical composition according to claim 8, wherein said topically transdermal patch is liquid reservoir type controlled-release patch containing of non-permeable matrix liquid drug, rate-moderate membrane, PSAs and release layer, wherein: the non-permeable matrix is one or more substances selected from a group consisting of the following: polyethylene, PVC, nitroglycerin, polydimethylsiloxane, PVP, polyvinyl alcohol, complex of polyethene oxide, polyethylene glycol, polyethylene glycol monomethyl ether or polyethylene glycol dimethyl ether, polyethylene glycol succinate and vitamin E TPGS, wool and cotton;

said rate-moderate membrane is selected from a group consisting of membrane of copolymer of the ethylene and vinyl acetate, membrane of polyurethane or membrane of glycol diacetate; and said PSAs is selected from a group consisting of polysiloxane pressure-sensitive gum or polyacrylate pressure-sensitive gum.

12. The pharmaceutical composition according to claim 11, wherein said matrix is polyethylene or PVC.

13. The pharmaceutical composition according to claim 8, wherein said topically administered transdermal patch is the matrix type controlled-release patch, the auxiliary of drug adhesive matrix in the patch is selected from a group consisting of PVC, polyacrylate, polydimethylsiloxane, PVP, polyvinyl alcohol, water gel madeof gel, PVP, complex of PVP and polyethylene oxide, polyethylene glycol monomethyl ether or polyethylene glycol dimethyl ether, polyethylene glycol succinate and VE TPGS.

14. The pharmaceutical composition according to claim 13, wherein the auxiliary of drug adhesive matrix is polyacrylate.

15. The pharmaceutical composition according to claim 5, wherein said preparation form is tablet, pill, dispersed powder, capsule, granule, emulsion, solution, suspension, syrup, solid suppository for vaginal or rectal administration.

16. A method to prepare the composition of claim 9, comprising of the following steps:

weighing an appropriate amount of compound of formula I as the active ingredient and pulverizing into fine powder, into which add water phase, oil phase, surfactant and needed carriers to mix well;

continuing to add the pulverized drug powder to blend to make into microemulsion;

adding an appropriate amount of rate-mederated membrane and pressure-sensitive adhesive to stir well;

degassing by heat preservation using water bath and spreading on a polyethylene matrix; and drying and cutting to little pieces to give said solid reservoir type controlled-release patch.

* * * * *